US005749361A

United States Patent [19]
Mateyko

[11] Patent Number: 5,749,361
[45] Date of Patent: May 12, 1998

[54] SOFT-TISSUE INJURY ASSESSMENT SYSTEM

[76] Inventor: Peter T. Mateyko, 608 Drymen Cres., Mississauga, Ontario, Canada, L5G 2P1

[21] Appl. No.: 489,678

[22] Filed: Jun. 13, 1995

[51] Int. Cl.$^6$ ........................................... A61B 5/00
[52] U.S. Cl. ................... 128/653.1; 128/660.03
[58] Field of Search ............... 128/653.1, 660.03, 128/731–733, 739–744, 905; 601/2–3; 606/23

[56] References Cited

U.S. PATENT DOCUMENTS

| | | | |
|---|---|---|---|
| 4,681,121 | 7/1987 | Kobal | 128/731 |
| 4,913,160 | 4/1990 | John | 128/731 |
| 5,143,081 | 9/1992 | Young et al. | 128/741 |
| 5,191,896 | 3/1993 | Gafni et al. | 128/742 |

*Primary Examiner*—Francis Jaworski
*Attorney, Agent, or Firm*—Our Pal(R) Asija

[57] ABSTRACT

A system for assessing soft-tissue injury in a subject. The system comprises means for applying energy internally to tissue of the subject in an inaudible and invisible manner, with no indications to the epidermal tissue of the subject as to when energy is being applied or how much energy is being applied. The applying means has an energy control mechanism for varying parameters of energy application. The system also comprises a subject response unit having input means controlled by the subject in accordance with perceived sensation in tissue acted upon by the energy applying means. The system also includes also data recording means for simultaneously recording parameters of energy application from the energy applying means and parameters of perceived sensation from the subject response unit. With the system, application of energy occurs invisibly and inaudibly at an internal level. The tissue is stimulated from within by the energy. This stands opposed to external energy application, such as with pushing and probing, wherein the force is transmitted to the tissue by external compression. If a valid injury exists, the system will show a positive correlation between the applied energy and subject response. Visually comparing a computer generated graph of the energy intensity versus subject response, synchronized in time, will easily identify any discrepancies between cause and effect.

16 Claims, 9 Drawing Sheets

SOFT-TISSUE INJURY ASSESSMENT SYSTEM

FIELD OF THE INVENTION

The present invention is related in general to the medical field. More specifically, the present invention is a medical diagnostic system for obtaining an objective and reliable assessment of soft-tissue (muscle and joint) injuries

BACKGROUND

Contemporary diagnostic imaging techniques are unable to determine, corroborate, or assess soft-tissue health in animate vertebrate entities. Accordingly, assessment of soft tissue damage has been limited to the somewhat crude "push and ask" method wherein subject sensations are noted while the tissue is externally probed. This method suffers in that it does not provide: a mechanism for accurately repeating the amount of energy used by the examiner on the same subject at a later date; quantitative measurement of the intensity of pain sensed in response to that mechanical pressure; or an indication of the temporal relationship between the application of energy and the onset or increase of discomfort or pain. In short, previous soft tissue assessment methods have not been objective.

A further problem with the "push and ask" method is that the mechanical force pressure has always been applied externally through the outer skin of a subject, thereby providing tactile and sensory clues to the examined subject as to the level of energy being applied to the injury by the examiner. A subject could easily match their response to the externally applied energy. This makes it quite easy for the examined subject to express discomfort, sensitivity, and/or pain from the force of the external pressure, even with no injury existing.

Accordingly, it is an object of the present invention to provide an objective method and system for assessing soft-tissue injury. It is a further object of the invention to employ a controlled, invisible, inaudible energy to internally stimulate soft tissue. Discomfort, as a direct result of this energy, is produced in traumatized or injured tissues, but not in healthy tissues (incorporated by reference, Anderson, T. P. et al. "An experimental study of the effects of ultrasonic energy on the lower part of the spinal cord and the peripheral nerves" Archives of Physical Medicine and Rehabilitation 32:71, 1951; Farmer, W. C. "Effect of Intensity of Ultrasound on Conduction of Motor Axons" Physiotherapy Vol. 48, pp. 1233–1237, 1968; Zankel, H. T. "Effect of Physical Agents on Motor Conduction Velocity of the Ulnar Nerve" Archives of Physical Medicine and Rehabilitation 457 pp. 787–792, 1966; Chusid, J. G. "Correlative Neuroanatomy and Functional Neurology", 1973)

SUMMARY OF THE INVENTION

The present invention is a system for assessing soft-tissue injury in a subject. The system comprises means for applying energy internally to tissue of the subject in an inaudible and invisible manner, with no indications to the epidermal tissue of the subject as to when energy is being applied or how much energy is being applied. Inaudible and invisible in this context means a method of transcutaneously delivering energy to subcutaneous soft tissues, without the stimulation being detectable by either the epidermis, or by normal, healthy, untraumatized subcutaneous soft tissue or visually or aurally detectable. In this case, "transcutaneously" means "through the skin, without detection in the skin through which it is passing. The applying means has an energy control mechanism for varying parameters of energy application. The system also comprises a subject response unit having input means controlled by the subject in accordance with perceived sensation in tissue acted upon by the energy applying means. The system also includes data recording means for simultaneously recording parameters of energy application from the energy applying means and parameters of perceived sensation from the subject response unit.

It should be stressed that with the present invention, application of energy occurs invisibly and inaudibly at an internal level. The tissue is stimulated from within by the energy. This stands opposed to external energy application, such as with pushing and probing, wherein the force is transmitted to the tissue by external compression. If a valid injury exists, the system will show a positive correlation between the applied energy and subject response. Visually comparing a computer generated graph of the energy intensity versus subject response, synchronized in time will easily identify any discrepancies between cause and effect. Comparison of applied energy from the applying means to the recorded parameters of response from the subject response unit is subjectively relative. That is to say, relative comparisons are completely valid, as long as the same subject is providing the response to the same stress. Congruities of perception, characterization, and differences of sensitization in different subjects, become common denominators when used with a controlled, measured, repeatable stress, and the same subject. In fact, the only change to the "common denominator" aspect of the "cause and effect" concept, is the health and integrity of the soft-tissue or joint being assessed. This therefore provides added utility for the system in that its uses are not limited to determining if a correlation exists between an undetectable application of energy and subject response, but also how successive applications of the same energy level at each successive examination session are perceived by the subject as the injured tissue heals.

The energy applying means can be any one of a variety of machines which can deliver the invisible and inaudible energy. Typical types of machines that may be used for energy applying means include, but are not limited to therapeutic ultrasound machines that enable the operator to alter the characteristics of the output energy, TENS (Transcutaneous Electronic Nerve Stimulator) machines, and therapeutic laser units.

The present invention envisions a variety of embodiments of the subject response unit, each having a particular circumstance for use. Single parameter indications of response by the subject being examined can be collected through the use of any type of knob, dial, lever, or other actuator operated through the voluntary physical action of the subject. This provides a resultant subject output of a discrete analog value, somewhere between zero and the upper limit value of the transducer. The larger the output value, the more intense is the subject's perceived sensation of discomfort.

It is also envisioned by the present invention that, a multi-parameter subject response unit can conveniently provide more information than a monopolar one, identifying both the intensity and the characteristic representation of the discomfort sensation, using multiple quadrants on an X-axis and Y-axis coordinate grid, with positive and negative values of an X-axis and Y-axis location possible. The purpose of a multidimensional subject response unit is the collection of more information about the sensory perception of the examined subject to the applied energy.

A third method of acquiring data from a subject is to derive data from an electroencephalograph, as evoked potential responses. The indications for the use of this method are instances when involuntary responses are desired or required. The evoked potential is collected as a complex waveforms from electrodes attached directly to the scalp, or other body parts of the subject under examination. The wave forms are collected in a specific temporal sequence, based on the application of the energy. The wave form is then processed through an appropriately programmed digital signal processor. The resultant processed wave form can have instances of increased amplitude at certain frequencies that are directly attributable to the application of the energy from the applying means. This form of data acquisition makes it possible for nonverbal or communication-impaired humans, as well as most other animate vertebrates, to respond to outside stimulation.

The present invention can also be used with humans: to assess the effectiveness of various forms of therapy for soft-tissue injuries; to assess the effectiveness of drugs; to assess the completeness of nerve-blocking means; to determine and locate the existence of unknown soft-tissue injuries; to quantify the severity of soft-tissue injuries or damaged joints; to monitor the long-term progress of various Repetitive Strain Injuries; to quantify the soft-tissue health of animate vertebrates; and in general to assess soft-tissue and joint afflictions in non-human vertebrates.

DESCRIPTION OF THE PREFERRED EMBODIMENT

Figure 1:
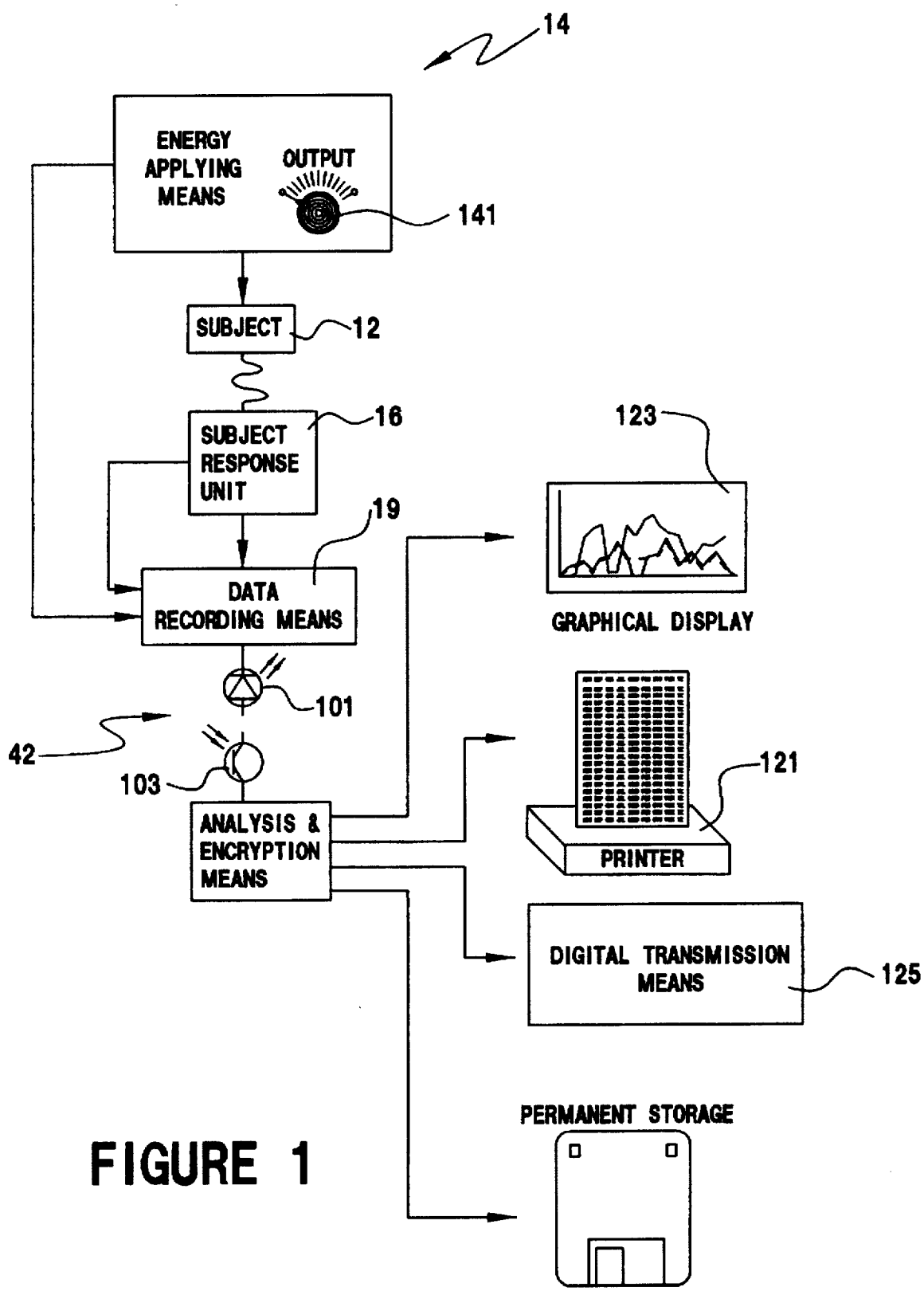
FIG. 1 is a block diagram illustrating the primary functional components of the system.

Referring now to the drawings wherein like reference numerals refer to similar or identical parts throughout the several views and more specifically to FIG. 1 thereof there is shown a system 10 for assessing soft-tissue injury in a subject 12. The system 10 comprises means 14 for applying energy internally to tissue of the subject 12 in an inaudible and invisible manner. The applying means 14 has an energy control mechanism for varying parameters of energy application. The system 10 also comprises a subject response unit 16 having input means 18 controlled by the subject 12 in accordance with perceived sensation in tissue acted upon by the energy applying means 14. There is also data recording means 19 for simultaneously recording parameters of energy application from the energy applying means 14 and parameters of perceived sensation from the subject response unit 16.

It should be stressed that with system 10, application of energy occurs invisibly and inaudibly from the external body surface to internal tissue. The tissue is stimulated from within by the energy. This stands opposed to external energy application, such as with pushing and probing, wherein the force is transmitted to the tissue by external compression Comparison of applied energy from the applying means 14 to the recorded parameters of response from the subject response unit 16 is subjectively relative. That is to say, relative comparisons are completely valid, as long as the same subject 12 is providing the response to the same stress. Congruities of perception, characterization, and differences of sensitization in different subjects, become common denominators when used with a controlled, measured, repeatable stress, and the same subject. In fact, the only change to the "common denominator" aspect of the "cause and effect" concept, is the health and integrity of the soft-tissue or joint being assessed. This therefore provides added utility for the system 10, in that its uses are not limited to determining if a correlation exists between an undetectable application of energy and subject response, but also how successive applications of the same energy level at each successive examination session are perceived by the subject as the injured tissue heals.

The energy applying means 12 can be any one of a variety of machines which can deliver the invisible and inaudible energy. Typical types of machines that may be used for energy applying means 12 include but are not limited to therapeutic ultrasound machines that enable the operator to alter the characteristics of the output energy, TENS (Transcutaneous Electronic Nerve Stimulator) machines, and therapeutic laser devices. These machines are available as items of common manufacture, and this invention will work with a plurality of them.

If using a therapeutic ultrasound machine (such as in described in U.S. Pat. Nos. 3,974,682, 4,128,012 or 4,257,270, incorporated by reference herein) the BNR rating of the transducer should be 4:1 or lower (approaching 1:1). Typically, acoustic energy ranging in frequency from 20 KHz to 20 MHz works best to stimulate soft-tissue or joint areas of the subject 12 and create manifestations of localized sensation in the soft-tissue or joint areas of the subject 12.

When using TENS or therapeutic laser, the use of pulsed or continuous wave trains of inaudible and/or invisible frequencies of electromagnetic energy from 10 Mhz to 375 THz (TeraHertz) work best to stimulate soft-tissue or joint areas of the subject 12 and create manifestations of localized sensation in the soft-tissue or joint areas of the subject 12.

The Subject Response Unit 16 is the variable apparatus required to obtain a response from the subject under examination, from the applied energy. The present invention envisions a variety of embodiments of the subject response unit 16, each having a particular circumstance for use. Single parameter indications of response by the subject 12 being examined can be collected through the use of any conventional type of knob, dial, lever, or other actuator operated through the voluntary physical action of the subject 12. This provides a resultant subject response output of a discrete analog value, somewhere between zero and the upper limit value of the transducer. The larger the output value, the more intense is the subject's perceived sensation of discomfort. The cessation of energy from the energy applying means 14 is generally expected to produce a zero response from the subject 12. All other responses are generally expected to be some form of discomfort, from barely discernible to intensely painful.

Figure 2:
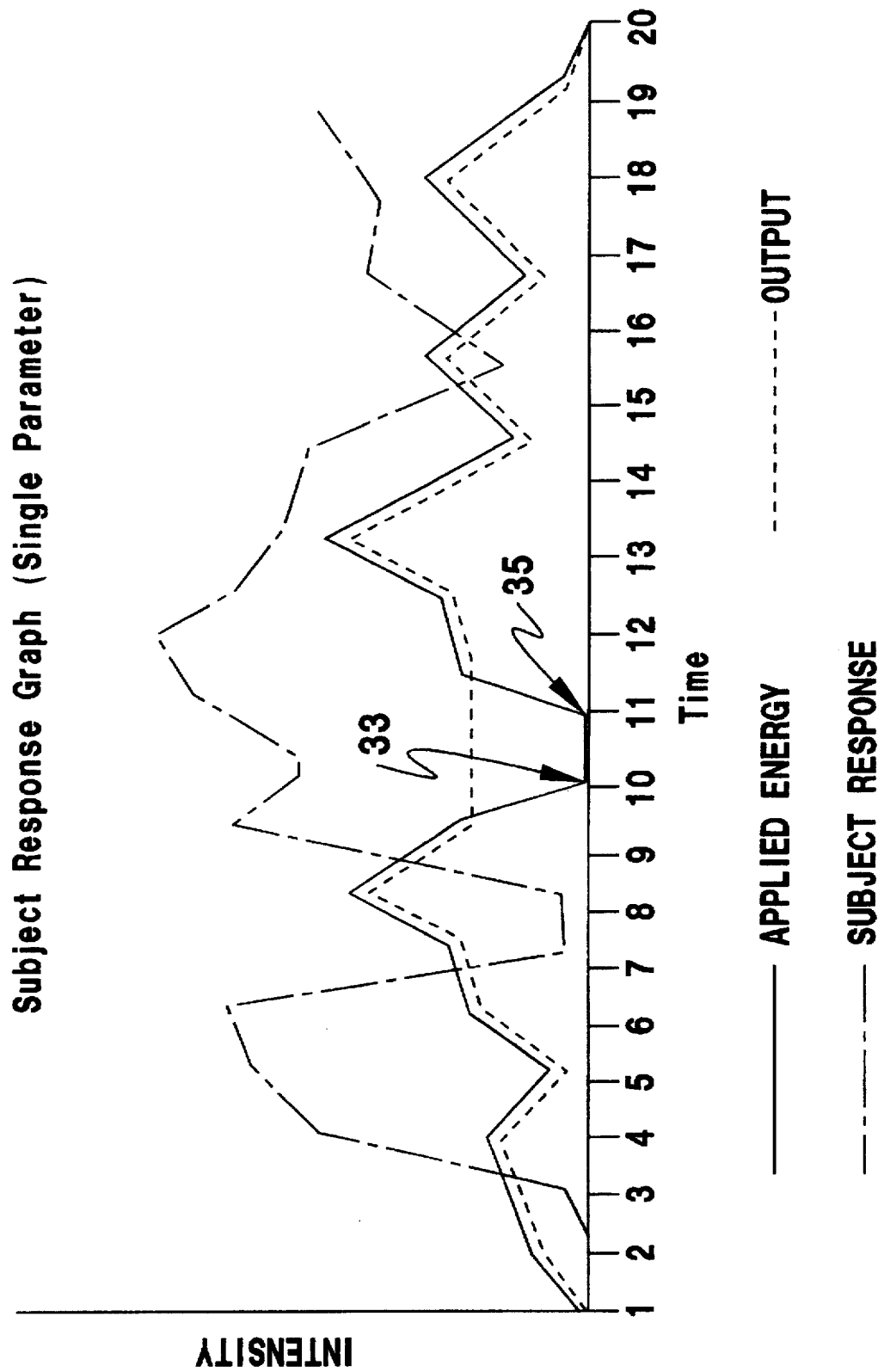
FIG. 2 is a graph showing the temporal relationship of parameters of energy application and parameters of perceived subject response.

FIG. 2 is a graph showing the temporal relationship between intensity of applied energy, subject response and actual output dial position of the energy applying means 14. The failure of the subject to be able to follow the changes in delivered power are indications that the subject is unable to detect the invisible/inaudible energy stimulus. As the only method the subject 12 has to follow the actual delivered power are his neurological response from the injured tissue, the graph illustrates a lack of injury of the tissue being assessed. Correlation's between the subjects' response and the Intensity control (indicated by the dashed line) without a correlation between the actual applied energy intensity, are indications that the subject 12 is attempting to match his/her response with the power control adjustments of the examiner. The points 33 and 35 on the x-axis identifies the span where the PAUSE control temporarily interrupted power application with out a change in the power output dial of the energy applying means 14.

Figure 9:
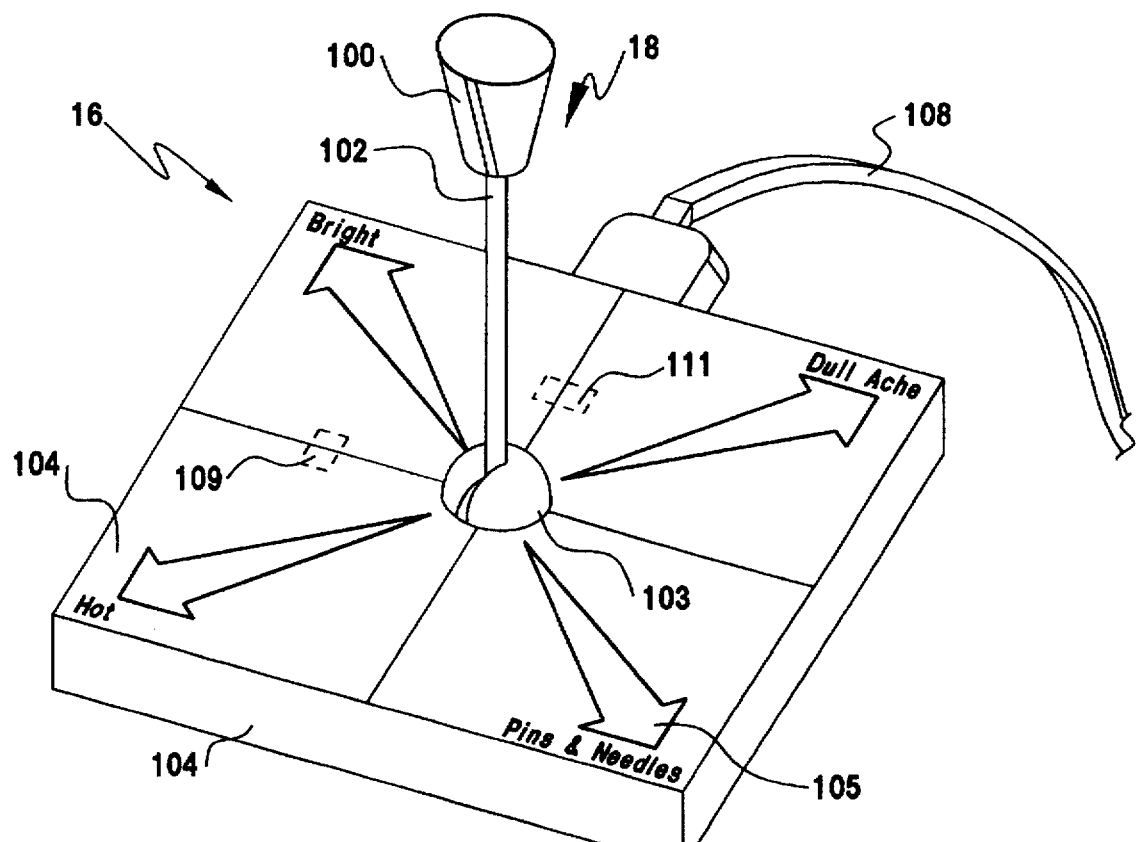
FIG. 9 is an illustration one embodiment of a multi-parameter subject response unit

As illustrated in FIG. 9, It is also envisioned by the present invention that a multi-parameter subject response unit 16 can conveniently provide more information than a monopolar one, identifying both the intensity and the characteristic representation of the discomfort sensation, using multiple quadrants on an X-axis and Y-axis coordinate grid, with positive and negative values of an X-axis and Y-axis location possible. This user response unit 16 is capable of providing multiple dimensions of response by the subject 12. It is comprised of a knob 100, shaft 102 and gimbal 103. The gimbal 103 is in communication with two transducers 109,111 which monitor the x and y positions of the shaft 102, respectively. The subjects use of the shaft 102 as a guide to the subjects moment to moment sensation response to the applied energy is directed according to graphical symbols 104, 105. A cable 108 carries the data to the input port to the data recording means 19.

Figure 3:
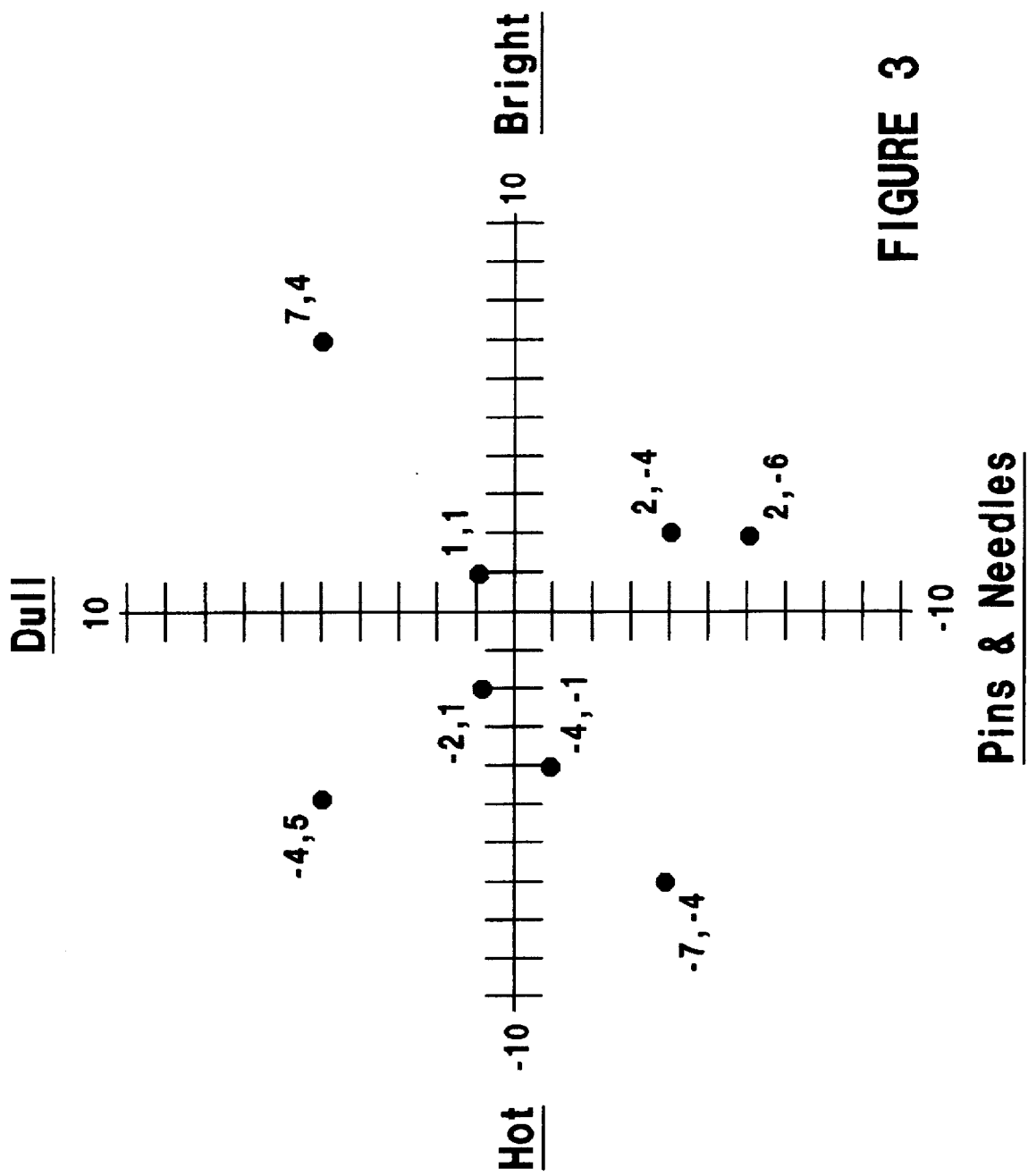
FIG. 3 is a diagram showing multi-parameter vector data of perceived sensations from a subject.

FIG. 3 indicates a Cartesian quadrant positioning of different intensities and manifestations of discomfort, as recorded using a multidimensional subject response unit 16. With the origin in the center of a Cartesian plot, each quadrant represents a separate domain of sensation; the vector angle of the response into any quadrant represents the degree of sensory characterization of the discomfort by the subject, while the vector distance from the origin represents the perceived intensity of the sensation by the subject. An instantaneous reading of 1,1 might represent a low intensity sensation of a partly "bright", partly "dull" sensation, while the reading of 7,4 (which is in the same quadrant), might represent a more intense discomfort that is characteristically more "bright" and less "dull". An instantaneous reading of −2,1 might represent a low intensity sensation of a sensation somewhere between "dull" and "hot", while the reading of −4,5 (which is in the same quadrant), might represent a more intense discomfort of a sensation that is characteristically more "dull". An instantaneous reading of −4,−1 might represent a low intensity perception of a "hot" sensation, while a reading of −7,−4 might represent a more intense perception of a "hot" sensation. An instantaneous reading of 2,−4 might represent a low intensity perception of a "prickly" sensation, while a reading of 2,−6 might represent a more intense perception of the same "prickly" sensation.

The purpose of the multidimensional subject response unit 16 is the collection of more information about the sensory perceptions of the examined subject 12 to the applied energy. An example of another information parameter is the characterization of the sensation (such as hot, sharp, dull, prickly, etc). The multidimensional subject response unit 16 can be constructed similar to the monopolar response unit, except that the manual input means 18 has a default or starting position of zero, and is located in the center of its range of travel. Like a conventional joystick, the subject response unit 16 can have two transducers 109,111 situated such that one transducer operates in a plane of travel perpendicular to the first, with the origin of both transducers 109,111 being coincidentally located. The position of any transducer is described as an analog value, stored in number of bytes. Each byte may represent a positive or negative value.

A third method of acquiring data from a subject 12 is to derive data from an electroencephalograph (EEG), as evoked potential responses. The indications for the use of this method are instances when involuntary responses are desired or required. (see U.S. Pat. No. 4,421,121, entitled "Method and Apparatus for obtaining Non-Encephalic Referential EEG" and U.S. Pat. No. 4,421,122 entitled "Brain Electrical Activity Monitoring"). An EEG 97 is shown in FIG. 4.

The evoked potentials are collected as a complex waveform from conventional EEG electrodes attached directly to the scalp, or other body parts of the subject 12 under examination. The waveforms are collected in a specific temporal sequence, based on the application of the energy. The waveform is then processed through an appropriately programmed digital signal processor. The resultant processed waveform can have instances of increased amplitude at certain frequencies that are directly attributable to the application of the energy from the energy applying means 14. These instances of increased amplitude are indications of discomfort. An increase in stress also produces an involuntary amplitude increase in the waveform of the subject 12. This form of data acquisition makes it possible for nonverbal or communication-impaired humans, as well as most other animate vertebrates, to respond to outside stimulation. Common indications for the use of this type of subject response unit 16 would be the assessment of non-lucid injured humans, pathological liars, injured animals, subjects who will not voluntarily respond, or humans who are too young to comprehend the concept of the examination.

Critical to the process and procedure for using the system 10, are issues that deal with the acquisition and analysis of data for each instant of time. The temporal relationship between all the controls, status indicators, and responses is paramount; for that reason, it has been determined that an electronic interface 22 having simultaneous latching data buffers 24 is preferred.

Figure 4:
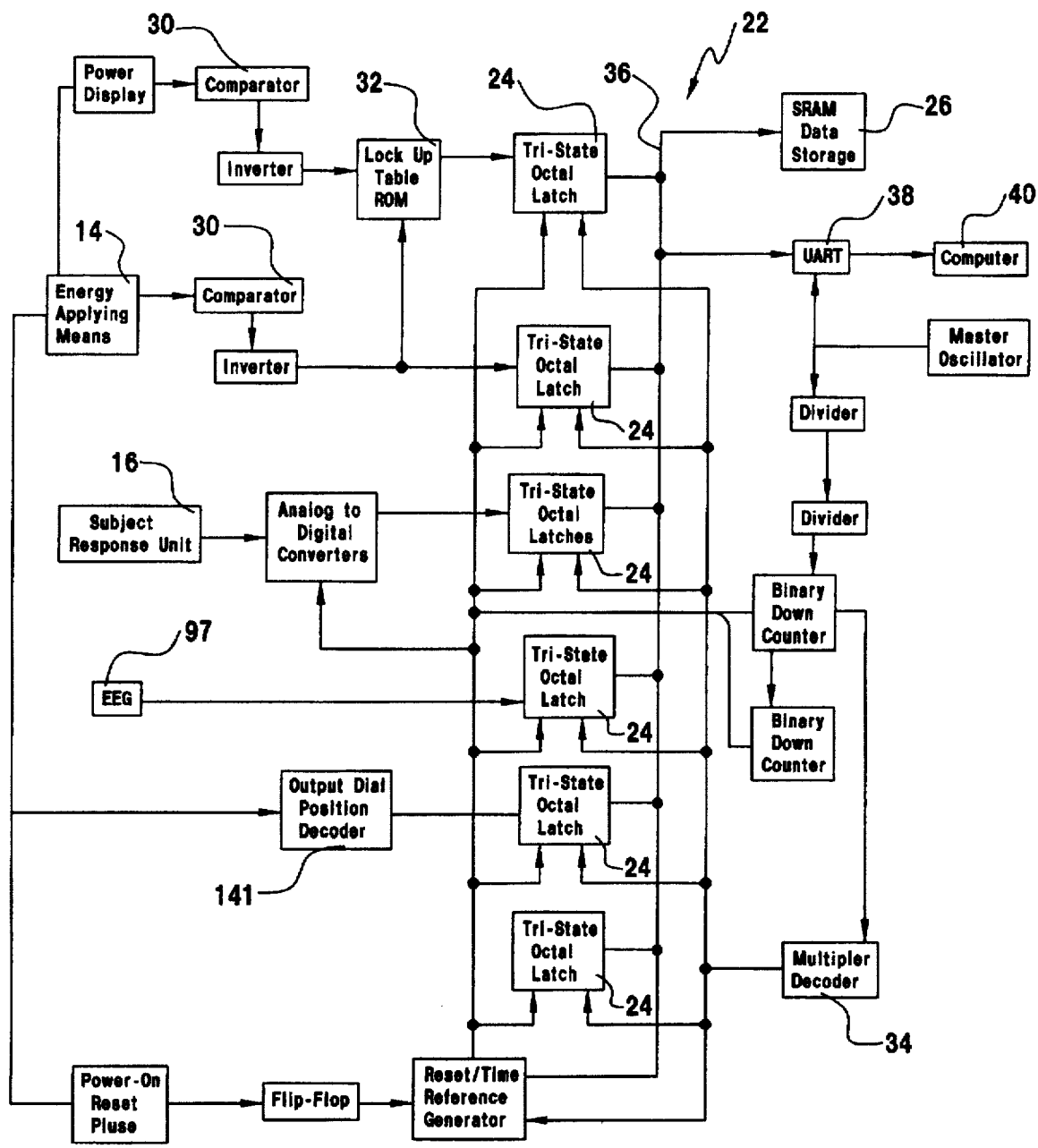
FIG. 4 is a block diagram illustrating an embodiment of the electronic interface for obtaining real-time pertinent data concerning the applied energy and the examined subject response for a sequence of definable instants of time.
Figure 5:
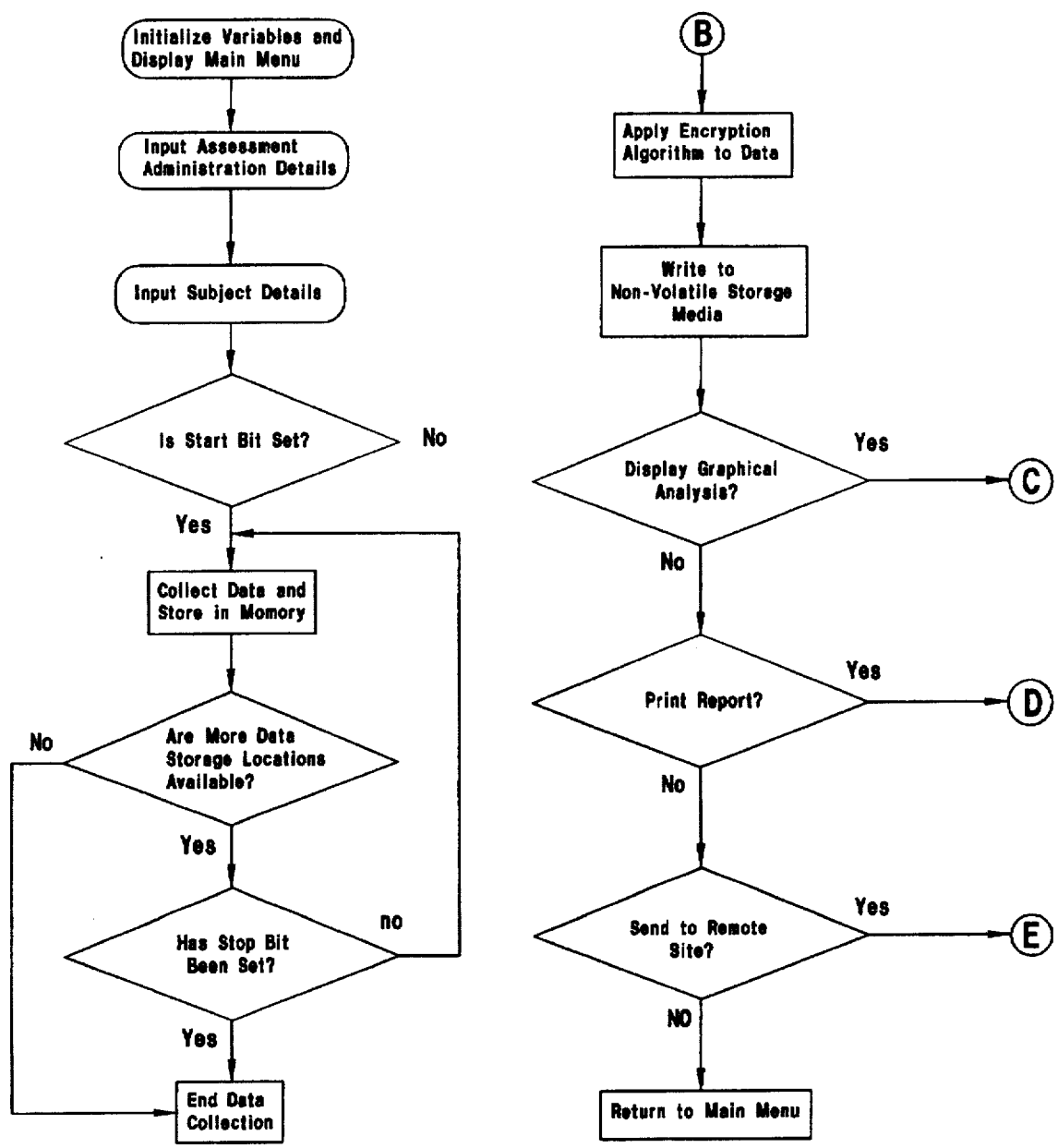
FIGS. 5–8 are logic flowcharts representing the steps needed for the computer to acquire and store data, load the data for review, process the data for display, determine if the data has been altered, produce hard copy, and transmit/receive data to/from other sites.
Figure 6:
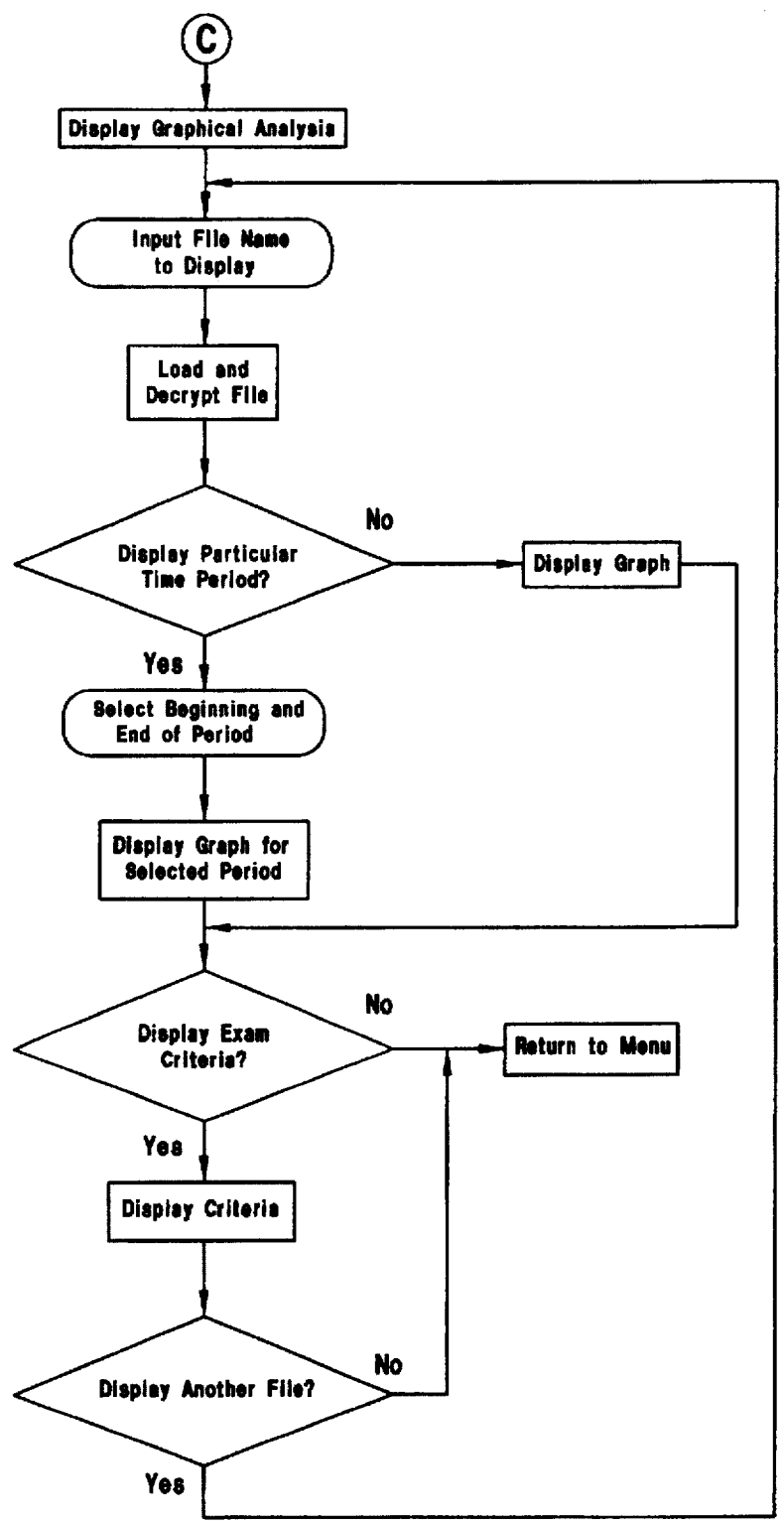
Figure 7:
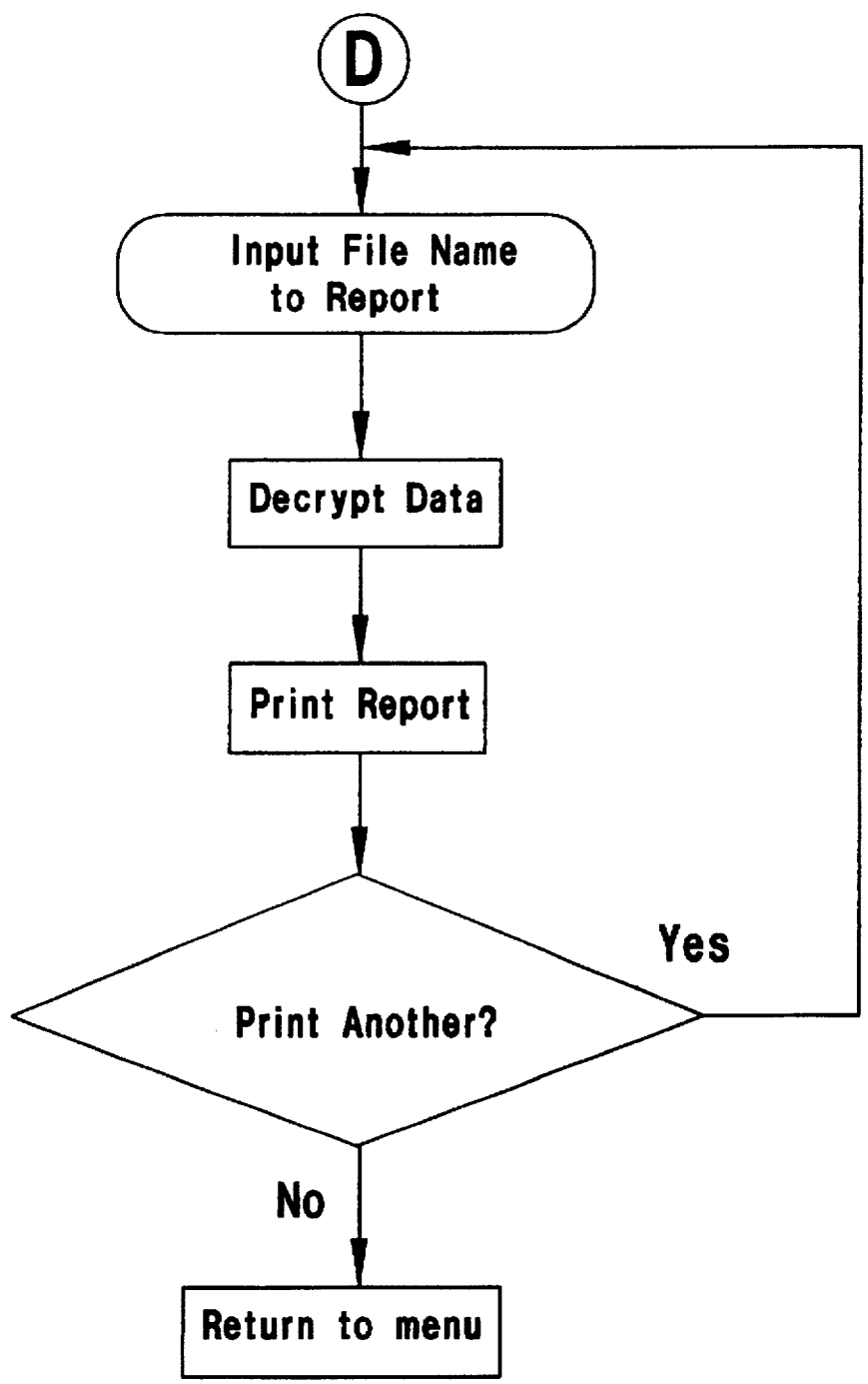
Figure 8:
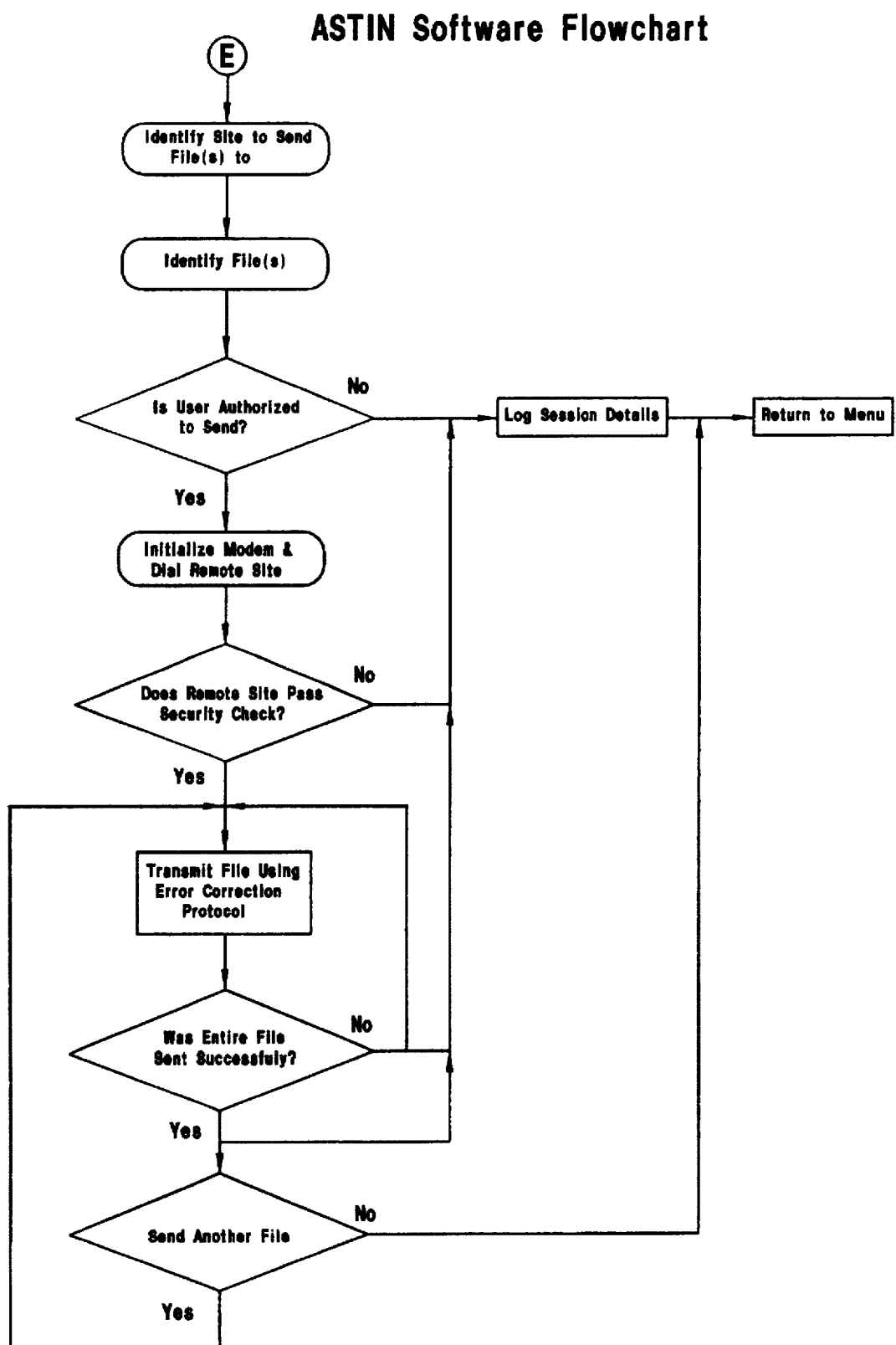

FIG. 4 illustrates an embodiment of an electronic interface 22 having a plurality of latching buffers 24. Analysis of the recorded data provides the time offset of the "cause and effect", or "stress and response", cycle. The electronic interface 22 is constructed in a manner, such that it does not impinge on the operation of the energy applying means 14. All electrical connections are performed parasitically, so as not to affect the operation of any controls. The electronic interface 22 provides a means of and method for obtaining all the real-time pertinent data concerning the applied stimulus and the examined subject response for a sequence of definable instants of time.

This recorded data may include, but is not limited to: 1) the frequency, time, and amplitude characteristics of the applied energy and wave train; 2) the quality of energy transfer coupling between the applying means and the subject, in terms of either delivered energy or wasted energy; 3) the length of time of applied energy; 4) the status of energy production at any instant in time (whether the machine is actively producing output energy or is in the pause mode); 5) the units of measure of the delivered energy; 6) the measure of the delivered energy, in power density, delivered power, voltage, amperage, or other units as may be practical; and 7) the absolute positions of any controls and status indicators that can be used to adjust, alter, or identify the output characteristics of the applied energy. The electronic interface 22 also accepts information produced by the subject response unit 16, and may convert it into an appropriate format. The response from the examined subject may be obtained from voluntary or involuntary physical or psychological manifestations or actions. The results of the information from the interface may be stored in Non-Volatile Random Access Memory 26 connected to the interface 22, or may be sent to memory of a computer 40.

When retrofitting the present invention to existing power applying means units (i.e. conventional ultrasound devices), frequently, the parameters of power application can be gathered as detected from the status of the unit's existing LED or LCD displays, using differential comparators 30. In the case of LED displays, it has been experienced that most LED displays are multiplexed at a relatively high rate, to prevent the ocular sensation of flickering. Each segment is therefore necessarily forward-biased (to illuminate) for a brief time. In an analog circuit, it can be continuously detected when each LED segment becomes forward-biased. If forward-biased, it is pulse-stretched to the detected "ON" state, for presentation to a read only memory 32. This effects real-time detection of all LED segments, for decoding by the Read-Only Memory 32. The Read-Only Memory 32 is programmed with the values of all combinations of illuminated LED segments, and their corresponding digital output data values. The output of the Read-Only Memory 32 is then sampled in real-time and fed to a latching buffer 24. Other data is also sampled in real-time and fed to the other latching buffers 24. At the same instant in time, all the buffers 24 are latched simultaneously. A decoder 34 then selects each latch 24 in sequence, and enables its output to a data bus 36 connected to an output driver, such as a universal asynchronous receiver transmitter 38. The UART 38 latches each byte of data sequentially, and transmits the byte in serial format to a personal computer 40 located at the opposite end of the data transmission link.

As illustrated in FIG. 1, there can be data transmission means 42 for allowing the transfer of data from the interface circuit 22 to a computer 40. The data transmission means 42 can be of any desirable construction such as a hardwired or wireless means of parallel or serial data transmission. FIG. 1 illustrates for instance a infra-red communications link 101 and infrared receiver 103. Alternatively, a hard-wired serial data port that is capable of driving a common RS-232C serial port on a computer is one of the least expensive, most common manifestations of such a data transmission means 42.

A computer 40 with associated software program can be used for the tasks of acquiring, securing, storing, retrieving, integrating, displaying, printing, receiving or transmitting the data from the assessment procedure, and providing administrative or self-diagnostic services. Before the examination and data collection commences, the examiner initiates the software program, and is prompted on-screen to enter a number of items of information regarding the subject being assessed, and the characteristics of the applied energy used for the examination. When this information has been properly recorded, the software program then prompts the examiner to proceed with the application of the energy. The software program commences the data collection as soon as energy application commences, as indicated by a specific data sequence.

The software reads and decodes the multiplexed input data stream. As the input data are acquired, they are constantly monitored to detect the status of specific bits that indicate the commencement or the cessation of the data items. Data collection may also be programmed to conclude after a preset number of data points in the multidimensional data array are filled by incoming data. Alternatively, data collection can be programmed to pause whenever a specific number of data points are filled, whenever the PAUSE mode is activated, or when there is a sudden cessation of certain data in the data stream. The software running on the receiving computer writes the incoming data to the appropriate locations in a multidimensional data array in random access memory. When the data collection is terminated, the software program allows the examiner to select a new or default file name under which the data is stored. Unseen by the examiner, the computer system: time stamps that record; the time of the original programming of the examination; and the time of the completion of the data collection. This data also become part of the record.

After the data has been collected and the examination is concluded, the software can apply a secure, multiple-iteration encryption algorithm to the data, and write out the data in a serial format to a permanent storage medium, such as a computer floppy diskette. The purpose of the encryption is several fold. First, the encryption makes the data completely nonsensical to a human reader. This provides security for reasons of privacy, and security from tampering. With most systems used to test or assess a situation to determine fact, there exists a strong temptation on the part of cheaters to change the outcome of the test. Raw data is never available for change after it has been collected. Raw data remains in a form that is nonsensical to a human. Thus, if the raw data were to be inadvertently available to an unauthorized person, it would be meaningless. This provides the first level of protection from tampering; because a potential violator is unable to see any of the decrypted data, it is impossible to know what to change. A second level of protection is provided to guarantee data security. If any piece of data associated with this file is changed, the system 10 will sound and display an alarm and message, and will not allow access for assessment or display. The data file contains not only the data acquired from the "energy application/response" cycle, but also demographic and vital statistic information concerning the subject 12, the insurance case and file number, the date, time, and duration of the examination, the examiners name, the characteristics of the applied energy used in the course of the examination, and other pertinent details.

As illustrated in FIG. 1, the software can facilitate transfer of this graphical information to printers 121, plotters, data files, or audio sequences. The software can also allow for the viewing on display means 123 which can be in a tabular format, indexed by time. The acquired data can be represented as a polyphonic sound sequences. The software can facilitates the automated transmission and reception of the acquired data files from one site to another with data transmission means 125. The software logs outbound transmissions for security purposes, and also logs all attempts by any user to initiate the software. The software is copy-protected, and requires password authentication before it will commence operation for each authorized examiner, in addition to the presence of a digital locking mechanism.

In the operation of the preferred embodiment, before the assessment can be performed on a subject 12, it is required that a preliminary physical examination establish the potential subject's neurological functions, broken bones, or any other medical condition which might be affected by the use of the applied energy. Firstly, the examiner who is to conduct the examination, initiates the previously described software program on a conventional personal computer 40. The software prompts the examiner to enter demographic subject information, insurance or other claim information, and other details related to the administration, protocol, and identification of the assessment and examiner. Next, the software queries the examiner for the specifics of the: structure, duty cycle, frequency, voltage, current, and other details of the applied stimulation modality to be used. The examiner defines the interval at which data is to be recorded (the sample rate), as "N" seconds. It has been found that values of "N" ranging from $\frac{1}{32}$ to 5 seconds are appropriate. When the examiner has completed all the queries posed by the computer program, the computer 40 then enables or "arms" the data collection system. The data collection system waits in this "ready" mode, until it detects the delivery of energy into the subject 12 being examined. One protocol established for the proper operation of one type of assessment session using the therapeutic ultrasound form of the energy applying means 14 is for the examiner to place the transducer of the energy applying means 14 (after preparing the subject to be examined with the appropriate coupling gel) at the location of the supposed injury, or area to be examined. The examiner, if using a therapeutic ultrasound machine would use (for example) a 1 MHz frequency wave of continuous duty cycle, and an initial setting of 0.6 W/cm2. The examiner, places the transducer at the examination site, and commences the delivery of power. The delivery of energy into the examined subject 12 is signaled by a response from the electronic interface 20 of the invention. When a "Start" control is activated on the applying means 14, the energy delivery commences. The examiner slowly moves the transducer in a circular fashion, taking about 3 seconds to complete one circular path of approximately 1" diameter. The speed of the circling is determined by the BNR of the transducer head, in the case of using a therapeutic ultrasound machine. A BNR of 4:1 uses a circle time of 3 seconds; a BNR of 1:1 does not usually require any circulation of the transducer. Three complete rotations of 3 seconds each, taking about 10 seconds in total are required to properly stress the injury. The output energy level is then increased by the examiner, by 0.3 w/cm2, and the area is circled three times, again. This procedure is repeated until the subject 12 being examined responds that some sensation is perceived.

The subject 12 being examined operates by either: deliberate voluntary physical control actions; electroencephalograph (EEG) activity; or other means, any of several different styles of subject response units 16 suitable for the subjects cognitive and manipulative capabilities. A voluntary-type subject response unit 16 quantifies on a (monopolar or Cartesian) scale of appropriate resolution, the subjects response to the level of discomfort or pain caused by the stimulation, as it is applied. An involuntary-type subject response unit could use an EEG signal mathematically transformed into discrete wave forms of specific frequencies by a DSP. These waveforms would, in turn be analyzed to determine unique instances that identify the subject's response to either a change in the energy application intensity, a change in position of the site where the energy is being transferred from the energy applying means 14 into the subject being examined, or a response from the subject due to total delivered energy. At the point of first response by the subject, the examiner notes the power level of the applied energy, and engages the "PAUSE" mode of the machine. After waiting 60 seconds in the "PAUSE" mode, the examiner next reduces the output power level to 0.5 W/cm2 less than the subject responded to earlier. Again, moving the transducer in small circles at the three second revolution rate, on the site of the injury and confirming good coupling, the examiner moves the output intensity control 141 of the energy applying means 14 at an appropriate rate of change from that reduced output level, to a point at least 0.5 w/cm2 (to a total of 1.6 W/cm2) above the level that produced the first response. The examiner may proceed to slowly and continuously change the delivered energy level within this range, continuously altering the output power.

At several times during this examination, the examiner should also engage the "PAUSE" mode for at least 10 seconds per instance. Investigations indicate that most human subjects 12 are able to respond to the applied energy in as little as a fraction of a second for "bright" pain, to several seconds for a "dull ache". The sensations cease as quickly as they commence, so the subject's response should change rapidly when the "PAUSE" control is engaged. Every N or Nths of a second, data from all sources are simultaneously latched, and sent in serial or parallel format to a multidimensional data array. Data changes are transmitted in real-time, and are latched and record delivery N seconds, until either the examiner feels that a thorough examination has been performed and the "Stop" button is pressed, or when the data array has been filled. For instance, data can be collected in 0.25 second increments for 15 minutes, or for a similar matrix size.

The present invention also envisions situations where numerous points on a subject 12 are to be examined. When the energy applying means 14 is active, but the delivered output energy suddenly drops to zero, we can conclude that the transducer delivering the energy is being moved from the present location to another location. If the locations have been predetermined, the software can prompt the examiner to proceed to the next location. Data is stored for each location at the appropriate place in the data set. Similarly, if stress is to be applied at each location for a specified time period, the computer 40 can measure this time, and prompt the examiner when that time has elapsed. A sudden large increase or decrease in energy transmission due to changes in coupling is the signal that transducer contact with the body being examined has been radically changed.

After all data is collected, the examiner is able to view the collected data in graphical, textual, or hard copy formats. Data collected previously, or data collected at other sites can be also be loaded into the computer 40. The display function of the system may be operated without any other assessment hardware, if used only to view data. Before data is loaded into the computer 40, data integrity operations are first automatically performed, that determine whether the data has been altered. Any detected alterations to the data cause a notice to appear on the screen, and an audible warning to sound, indicating that the data integrity of that file has been violated, and the software will not allow the data to be loaded for display of any type. If the data set has not been altered, it is allowed to load into the computer memory, and becomes available for display. A graphical display 50 could show the following items of information: parameters entered by the examiner by the initial software prompts before the start of the assessment; the length of elapsed time for the entire assessment procedure; the correlation of the applied energy from the energy applying unit, the responses of the vertebrate to the invisible, inaudible energy, and time. The software also allows for any time segment of the examination data to be expanded in a horizontal format, until only one segment of time occupies the entire visible X-axis of the display. It is also possible to switch between the demographic information entered at the start of the examination and the graphical display, at the touch of one key.

A positive correlation produces an "evoked potential" response from the subject 12 under examination; that is to say, the response is evoked by the application of the invisible, inaudible energy. If a valid injury exists, the graphical display 123 will show a positive correlation between the applied energy and subject response. If the only correlation is between the position of the output power control 141 and the subject response, then it can be determined that the output energy has not provided a discomfort response (but the position of the output power control has). It is not possible for correlation's to exist independently for both the output control position and the delivered energy level, as the "PAUSE" mode disconnects the link between these two variables. If the "pause" mode was engaged and the subject still indicated a discomfort response that did not rapidly decline (or rapidly increase when the "PAUSE" was released), then the examiner has confirmation that the subject 12 is either unable to respond to the delivered energy, or that an injury does not exist. As the preliminary physical examination has established the neurological integrity of the patient, the remaining fact is that the subject 12 has no soft-tissue or joint injury at that location.

The applications of the system 10 include the detection and location of injured soft tissues, and the single most common situation for its use is presumed to be the objective determination of whiplash injury and complaints of unsubstantiated lower back pain. It should be appreciated that the present invention can also be used: to assess the effectiveness of various forms of therapy for soft-tissue injuries; to assess the effectiveness of drugs; to assess the completeness of nerve-blocking means; to determine and locate the existence of unknown soft-tissue injuries; to quantify the severity of soft-tissue injuries or damaged joints; to monitor the long-term progress of various Repetitive Strain Injuries; to quantify the soft-tissue health of animate vertebrates; and in general to assess soft-tissue and joint afflictions in vertebrates.

Although the invention has been described in detail in the foregoing embodiments for the purpose of illustration, it is to be understood that such detail is solely for that purpose and that variations can be made therein by those skilled in the art without departing from the spirit and scope of the invention except as it may be described in the following claims.

I claim:

1. A system for assessing soft-tissue injury in a mammalian subject comprising:
    a) a means for applying ultrasound energy as internally to tissue of the subject in an inaudible and invisible manner;
    b) an energy control means for varying parameters of said ultrasound energy connected to said applying means;
    c) a subject response unit having an input means adaptable for control by the subject in accordance with perceived sensation in tissue acted upon by said ultrasound energy applying means; and
    d) a data recording means for simultaneously recording parameters of the ultrasound energy application from said ultrasound energy applying means and parameters of perceived sensation from said subject response unit, said data recording means in communication with said ultrasound energy applying means and said subject response unit.

2. The system for assessing soft-tissue injury of claim 1 wherein said ultrasound energy applying means comprises a means for directing a controlled amount and specific composition of said ultrasound energy into the tissue of the subject.

3. The system for assessing soft-tissue injury of claim 1 wherein the input means of said subject response unit receives a single parameter input from said subject.

4. The system for assessing soft-tissue injury of claim 3 wherein said single parameter is digital binary.

5. The system for assessing soft-tissue injury of claim 3 wherein said single parameter is analog.

6. The system for assessing soft-tissue injury of claim 1 wherein the input means of said subject response unit is designed to receive a multi-parameter input from said subject.

7. The system for assessing soft-tissue injury of claim 6 wherein said multi-parameter is two parameter joy stick.

8. The system for assessing soft-tissue injury of claim 1 wherein the input means of said subject response unit comprises an electroencephalograph for automatically detecting electromagnetic waveforms internally generated by said subject.

9. An apparatus for assessing and curing soft-tissue injury in a human being as subject comprising:
    a) a means for applying energy transcutaneously internally as non-tactile stimulus to injured tissue which is transparent to surrounding healthy tissue of the subject;
    b) an energy control means for varying parameters of said energy connected to said applying means;
    c) a therapeutic laser unit connected to said means for applying energy;
    d) said therapeutic laser unit having a laser beam further including a means for directing the laser beam into the tissue of the subject internally and transcutaneously;
    e) a subject response unit having an input means adaptable for control by the subject in accordance with nonverbal perceived sensation in tissue acted upon by said energy applying means; and
    d) a data recording means for simultaneously recording parameters of the energy application from said energy applying means and parameters of perceived sensation from said subject response unit, and parameters of said laser beam, said data recording means in communication with said energy applying means and said subject response unit.

10. The system for assessing soft-tissue injury of claim 9 wherein said data recording means comprises an electronic interface and a computer, said electronic interface electronically connected to said energy applying means and said subject response unit to collect data therefrom, said interface electronically connected to said computer via a transmission means.

11. The system for assessing soft-tissue injury of claim 10 wherein the computer is programmed with operational and data collection software for storing data in a private encrypted format whereby attempts made to change any component of the data are detected and announced, and the use of the altered data is precluded by said software.

12. A method of assessing and monitoring soft-tissue injury in a mammalian subject comprising the steps of:
    a) applying ultrasound energy transcutaneously and internally to tissue of a subject in an audible and invisible manner;
    b) recording data associated with said ultrasound energy;
    c) recording a plurality of non-verbal subject response parameters as data associated with the subject's perceived response to said applied ultrasound energy; and d) comparing over time parameters of said energy application and the recorded parameters of said subject response.

13. The method of assessing and monitoring soft-tissue injury of claim 12 wherein said subject is a human and which additionally includes a step of directing a laser beam into the tissue of said subject such that the subject is unable to see or hear when said laser beam is in an active state.

14. The method of assessing and monitoring soft-tissue injury in mammalian subject of claim 12 wherein the recording step includes the step of collecting data form an electroencephalograph disposed in communication with said human subject.

15. The method of assessing and monitoring soft-tissue injury in a human subject of claim 12 including the step of displaying in a graphical format the temporal relationship between parameters of applied ultrasound energy and said human subject response.

16. The method of assessing and monitoring soft-tissue injury in a human subject of claim 12 wherein the recording step includes the storing of recorded test parameter data in encrypted format.

* * * * *